(12) United States Patent
Bauer et al.

(10) Patent No.: US 10,905,645 B2
(45) Date of Patent: Feb. 2, 2021

(54) METHOD FOR PRODUCING SHAPED FUNCTIONAL CELLULOSE ARTICLES WITH TARGETED RELEASE OF ACTIVE INGREDIENTS

(71) Applicant: smartpolymer GmbH, Rudolstadt (DE)

(72) Inventors: Ralf-Uwe Bauer, Rudolstadt (DE); Frank Meister, Rudolstadt (DE); Michael Mooz, Saalfelder Höhe (DE); Markus Krieg, Weimar (DE); Sabine Riede, Uhlstadt-Kirchhasel (DE)

(73) Assignee: smartpolymer GmbH, Rudolstadt (DE)

( * ) Notice: Subject to any disclaimer, the term of this patent is extended or adjusted under 35 U.S.C. 154(b) by 122 days.

(21) Appl. No.: 15/534,101

(22) PCT Filed: Dec. 9, 2015

(86) PCT No.: PCT/EP2015/079148
§ 371 (c)(1),
(2) Date: Jun. 8, 2017

(87) PCT Pub. No.: WO2016/091963
PCT Pub. Date: Jun. 16, 2016

(65) Prior Publication Data
US 2017/0333331 A1 Nov. 23, 2017

(30) Foreign Application Priority Data
Dec. 9, 2014 (DE) .................. 10 2014 018 139

(51) Int. Cl.
| | | |
|---|---|---|
| *A61K 8/73* | (2006.01) | |
| *D01F 1/10* | (2006.01) | |
| *C08B 1/00* | (2006.01) | |
| *D01F 1/02* | (2006.01) | |
| *D01F 2/00* | (2006.01) | |
| *C08L 1/02* | (2006.01) | |
| *A61K 8/02* | (2006.01) | |
| *A61K 8/06* | (2006.01) | |
| *A61K 8/25* | (2006.01) | |
| *A61K 8/42* | (2006.01) | |
| *A61K 8/58* | (2006.01) | |
| *A61K 8/67* | (2006.01) | |
| *A61K 8/92* | (2006.01) | |
| *C08K 3/36* | (2006.01) | |
| *C08K 9/04* | (2006.01) | |
| *D01F 2/02* | (2006.01) | |

(52) U.S. Cl.
CPC .............. *A61K 8/731* (2013.01); *A61K 8/027* (2013.01); *A61K 8/064* (2013.01); *A61K 8/25* (2013.01); *A61K 8/42* (2013.01); *A61K 8/585* (2013.01); *A61K 8/678* (2013.01); *A61K 8/922* (2013.01); *A61K 8/925* (2013.01); *C08B 1/003* (2013.01); *C08K 3/36* (2013.01); *C08K 9/04* (2013.01); *C08L 1/02* (2013.01); *D01F 1/02* (2013.01); *D01F 1/10* (2013.01); *D01F 2/00* (2013.01); *D01F 2/02* (2013.01); *D10B 2509/00* (2013.01)

(58) Field of Classification Search
CPC ..... D01F 1/02; D01F 1/10; D01F 2/00; D01F 2/02; C08K 9/04; C08K 3/36
See application file for complete search history.

(56) References Cited

U.S. PATENT DOCUMENTS

| | | | | |
|---|---|---|---|---|
| 5,085,856 A | * | 2/1992 | Dunphy | ............. A61K 8/375 424/401 |
| 5,153,066 A | | 10/1992 | Tanaka et al. | |
| 5,792,399 A | * | 8/1998 | Meister | ............. C08B 1/003 106/200.1 |

(Continued)

FOREIGN PATENT DOCUMENTS

| | | |
|---|---|---|
| DE | 69600181 T2 | 7/1998 |
| DE | 10 2004 014 704 A1 | 10/2005 |

(Continued)

OTHER PUBLICATIONS

T. Fornes et al., "Effect of organoclay structure on nylon 6 nanocomposite morphology and properties," *Polymer* 2002, vol. 43, p. 5915.

(Continued)

*Primary Examiner* — Susan T Tran
*Assistant Examiner* — William Craigo
(74) *Attorney, Agent, or Firm* — ProPat, L.L.C.; Cathy Moore

(57) ABSTRACT

Methods for producing cellulose articles having controlled release of active ingredient include dispersing pulp in aqueous direct solvent for cellulose to form a slurry. Organically modified or ion-exchange-activated phyllosilicate is homogenized in a direct solvent for cellulose with exfoliation by shearing, then mixed with the slurried pulp. A mixture of active ingredient and a lipophilic matrix material or a water-in-oil ("W/O") emulsion containing active ingredient is stabilized with thickener, converted into a gel-like paste, and mixed with the slurried pulp. Water is stripped from the mixture until all cellulose is dissolved, the mixture is formed into shaped articles, and dried. Exemplary active ingredients include cosmetic active ingredients, fat-soluble vitamins or apolar plant extracts. Domains of active ingredient and matrix material or emulsion containing active ingredient are present as fine divisions within the inventive articles. Exemplary shaped articles include functional fibers in knitted, woven and nonwoven fabrics; paper; foils and membranes.

21 Claims, 1 Drawing Sheet

(56) References Cited

U.S. PATENT DOCUMENTS

| | | | |
|---|---|---|---|
| 7,244,497 B2 | 7/2007 | Hartmann et al. | |
| 2006/0128867 A1* | 6/2006 | Marx | B82Y 30/00 |
| | | | 524/445 |
| 2011/0045078 A1* | 2/2011 | Kolbe | C08L 1/02 |
| | | | 424/488 |
| 2014/0350153 A1* | 11/2014 | Gawad | C08J 3/215 |
| | | | 524/188 |

FOREIGN PATENT DOCUMENTS

| | | |
|---|---|---|
| DE | 20 2004 021 259 U1 | 6/2007 |
| DE | 10 2006 046 358 B3 | 11/2007 |
| DE | 10 2007 054 702 A1 | 5/2009 |
| DE | 10 2010 007 497 A1 | 8/2011 |
| WO | WO 2005/017247 A2 | 2/2005 |
| WO | WO 2009 062 657 A2 | 5/2009 |

OTHER PUBLICATIONS

T. Fornes et al., "Nylon-6 Nanocomposites from Alkylammonium-Modified Clay: The Role of Alkyl Tails on Exfoliation," *Macromolecules* 2004, vol. 37, p. 1793.

N. Hasegawa et al., "Nylon 6/Na-montmorillonite nanocomposites prepared by compounding Nylon 6 with Na-montmorillonite slurry," *Polymer* 2003, vol. 44, p. 2933.

N. Fedullo et al., Nanocomposites from Untreated Clay: A Myth? *Macromol. Symp.* 2006, vol. 233, p. 235.

R. Wagener et al., "Rheologische Charakterisierung von Nanocompositen", 8. Rudolstädter Kunststofftag, May 21, 2003. Machine Translation.

P. Pötschke et al., "Rheological behavior of multiwalled carbon nanotube/polycarbonate composites"; *Polymer* 43: 2002, pp. 3247-3255.

\* cited by examiner

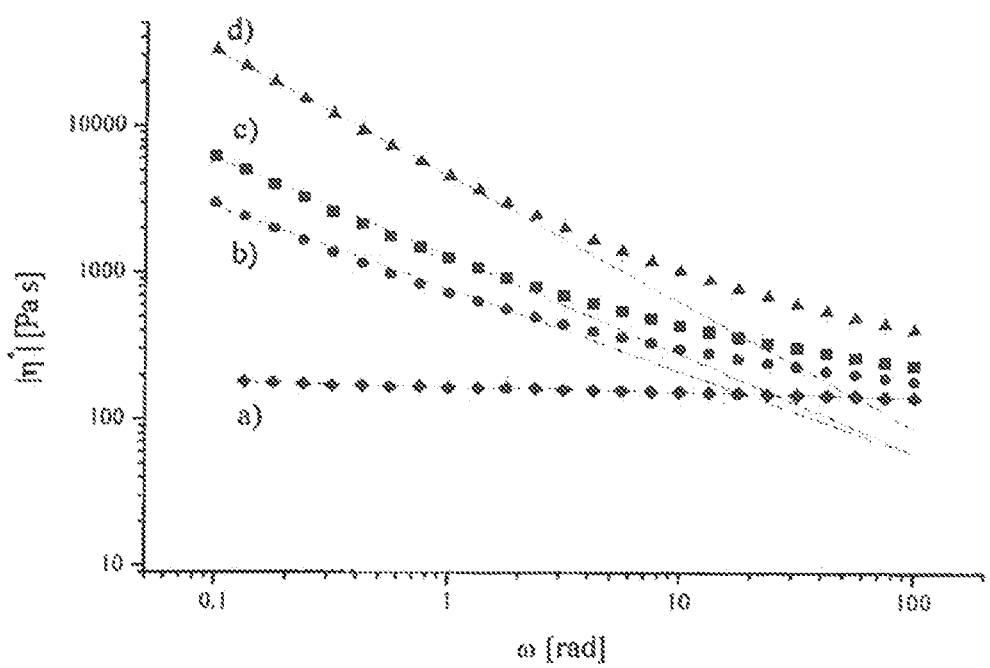

METHOD FOR PRODUCING SHAPED FUNCTIONAL CELLULOSE ARTICLES WITH TARGETED RELEASE OF ACTIVE INGREDIENTS

CROSS-REFERENCE TO RELATED APPLICATIONS

This application is being filed under 35 U.S.C. § 371 as a National Stage Application of pending International Application No. PCT/EP2015/079148 filed Dec. 9, 2015, which claims priority to the following parent application: German Patent Application No. 10 2014 018 139.1, filed Dec. 9, 2014. Both International Application No. PCT/EP2015/079148 and German Patent Application No. 10 2014 018 139.1 are hereby incorporated by reference herein in their entirety.

FIELD OF THE INVENTION

The invention relates to a method for producing shaped cellulosic articles featuring intentional release of active-ingredient inclusions. The active ingredients, or actives, in question are solid or liquid lipophilic actives, or they are W/O emulsions. The effect of this method is that the active ingredients firmly integrate in the shaped cellulosic article as the latter is being formed, yet the release of active ingredients is controllable in service.

BACKGROUND OF THE INVENTION

WO 2009 062 657 already describes a method for incorporating apolar substances such as, for example, phase change materials (PCMs) and/or apolar actives in shaped cellulosic articles. The prior art reviewed there concerns a lyocell process. An emulsion is prepared of cellulose in an aqueous direct solvent and the apolar substance. This emulsion is stabilized by incorporation of nanoscale, hydrophobic-modified fumed silica and/or the addition of sheetlike and/or elongate nanoscale particles. A method of this type ensures very firm integration of the apolar substances in the surrounding cellulosic matrix, very largely preventing any controlled release. A similar approach is described in DE 10 2006 046 358 A1. An intentional rate of releasing included actives is not taught.

Similarly, the direct incorporation of paraffin in meltable matrices of plastic is described in DE-C 10 2010 007 497 A1. Here the plastified mixture between 40 to 75% of paraffin and 60 to 25% of a polymeric supporting component consisting of 5 to 20% of a thermoplastifiable polymer, of 5 to 20% of a styrene block copolymer and of 0 to 20% of one or more additives is extruded through a die orifice at 130 to 220° C. and immediately on leaving the die quenched down to a temperature of 10 to 80° C. The main disadvantage with such a procedure is the low strength of the shaped article, the enormous extension of up to more than 500% and the need for a subsequent draw by a factor of 2 to 12. In addition, this method for incorporation in melts is not transferrable to methods for working with aqueous solutions, which generally have very ranch lower viscosities.

Multicomponent fibers having reversible thermal properties, available from Outlast Technologies Inc., and also fabricatable from cellulose via solution-spinning processes are described in the property rights U.S. Pat. No. 7,244,497 B2 and WO 2005/017 247 A2 and in the German utility model document DE 20 2004 021 259 U1. Fibers of this type are obtained by the use of inclusion structures, normally capsules that contain the PCM, or by sheath/core or island-in-the-sea structures, in each of which the PCM material is firmly enclosed by non-PCM material. Reversible thermal properties are the object, and they are obtained by a firm integration of the PCM materials in the composited article, they are thus unsuitable for an intentional release of active ingredients.

Lastly, the patent document U.S. Pat. No. 5,153,066 describes the integration of thermotropic dyes in a polymer matrix where inside and outside layers of the protective polymer matrix embed the dye phase. Again the object of the invention here is solely an effective way to prevent any release and/or early decomposition of the active ingredient due to external influences. Nor is any teaching provided as to how such stabilized compositions and/or W/O emulsions are usable for fiber production from a solution with subsequent extrusion, since these compositions and/or emulsions already represent the end product.

It is further known to use modified silicas for mechanical stabilization of keratinous substances/emulsions and/or for stabilization of W/O emulsions from DE69600181 T2 or DE 102004014704 A1. The main reason for their use resides in some enhancement of the interactions between different components of the mixture and hence is not related to a controlled release of active ingredients. Nor is any teaching whatsoever given for integrating these emulsions in fibers by the solution-spinning process under the high temperatures and shearing forces prevailing there.

The works of T. Fornes et al. (T. Fornes, P. Yoon, D. Hutter, H. Keskkula and D. Paul: Polymer 2002, 43, 5915) disclose the use of sheet-silicates having intercalated organic modifier molecules for controlling the degree of exfoliation in polymer mixtures or blends. Here even the structure of the intercalated modifiers on its own is capable of causing a series of structural changes to the polymer structure and/or the blend structure (cf. T. Fornes, D. Hutter and D. Paul: Macromolecules 2004, 37, 1793). The degree of separation between the individual platelets of silica may vary greatly in such a procedure. Whereas microcomposites dominate in the case of very little separation, the inclusion of molecules or molecular chains into the galleries of the silica platelets gives intercalated or else exfoliated structures, where the complete release of individual silica platelets results in a significantly changed interaction at the phase boundaries of the polymer components.

Hasegawa et al. (N. Hasegawa. H. Okaraoto, M. Kate, A. Usuki and H. Sato: Polymer 2003, 44, 2933) have additionally showed that even unmodified or minimally modified nanophyllosilicates, for example $Na^+$ montmorillonites (NaMMTs) may in certain circumstances be exfoliatable with just water or water vapor, this being stated to result in polymer structures similar to those obtained with the use of modified sheet-silicates. Water and/or water vapor may cause the NaMMTs to swell, making it possible, as with organomodified sheet-silicates, that molecular chains are subsequently able to intrude into the enlarged gallery spaces. N. Fedullo et al. (N. Fedullo, M. Sclavons, C. Bailly, J.-M. Lefebvre and J. Devaux: Macromol. Symp. 2006, 233, 235) have further shown that integrated molecular chains of PA 6 are in some instances very resistant to being washed off, and that even a multiple extraction with hexafluoroisopropanol (HFIP) did not achieve complete removal of the inclusions. Precise control over release behavior is thus not attainable in this way either. Using these sheet-silicates for stabilization of lipophilic substances or even W/O emulsions during the production of shaped cellulosic articles by the lyocell process has not been described.

SUMMARY OF ADVANTAGEOUS EMBODIMENTS OF THE INVENTION

Proceeding from the identified prior art, the invention addressed the problem of developing a method for integrating lipophilic compositions of active ingredients in the solid or molten state without the use of inclusion structures or carrier materials or as W/O emulsions into shaped cellulosic articles during the production thereof, so that the active ingredients form a fine dispersion in the shaped article and are not washed off during coagulation, which often takes place in an aqueous medium. Special difficulties result from the fact that the process of shaped article production from solutions often gives rise to the action of very high shearing forces capable of engendering a phase separation, and that the coagulation or the removal of the solvent frequently takes place in aqueous media where the solvent is washed off and there is a risk that the compositions of active ingredients are also washed off as well. When the inventive shaped cellulosic articles come to be used, which is in textiles, active ingredients shall be released in a controlled manner and the contained substances thus be sent to an intended application without having to accept the technical and economic disadvantages described in the prior art. The problem addressed by the invention was additionally that of active ingredients that are lipophilic yet have an affinity for moisture and are in a dissolved or dispersed form being stored in a laundering-resistant manner and delivered in a controlled manner to the surroundings of the shaped article over a prolonged period. The problem addressed by the invention was further that of reloading the functionalized shaped articles with highly volatile or thermally/chemically sensitive active ingredients during the in-service phase.

BRIEF DESCRIPTION OF THE FIGURES

FIG. 1 is a graphical illustration of a rheological study of various exemplary inventive cellulose solutions subjected to a range of shearing intensities and/or durations.

DETAILED DESCRIPTION OF ADVANTAGEOUS EMBODIMENTS OF THE INVENTION

The problem is solved according to the invention by a multi-stage method comprising:
a) dispersing pulp in a known, aqueous direct solvent, for example NMMO, ionic liquids, or optionally mixtures of organic liquids with the recited direct solvents, or DMAc/LiCl,
b) in a separate step of the method of a nanoscale sheet-silicate, optionally organomodified, or preactivated by ion exchange with alkali and/or alkaline earth metal ions of higher periods (e.g., $K^+$, $Ca^{2+}Al^{3+}$ ions), or by water, being homogenized with an aqueous solution of the direct solvent in an ULTRATURRAX® homogenizer and being exfoliated fully or partially, to a defined degree, by adjustment of shear rate (rotary speed) and shearing time, added to the furnish and mixed with the cellulose furnish,
c) in a further separate step of the method the active-containing lipophilic substance which was rendered flowable by heating if necessary, or the active-containing W/O emulsion is being stabilized by organic or inorganic thickeners and converted into a gellike paste, this paste likewise being added to the cellulose furnish and mixed at solvent-dependent temperatures up to 130° C. under agitation,
d) and thereafter a further distillation being effected to completely dissolve the cellulose, and
e) the resultant spinning solution being shaped by one of the known solution-spinning processes into shaped articles such as, for example, staple fibers, filaments, films or direct webs and optionally being by one of the known processes aftertreated, spin finished and dried.

Active-containing lipophilic substance is to be understood as meaning a mixture of active ingredient and a lipophilic matrix material. Active-containing W/O emulsions enable hydrophilic actives, dissolved in water or hydrophilic solvents, to be "packaged" in a lipophilic matrix as well as lipophilic actives. There are also processes where a W/O emulsion is "packaged" once more in a lipophilic matrix.

The solution-spinning process is preferably a lyocell spinning process, i.e., in most cases the solution-spinning process will be a 'dry-wet spinning process'.

Nanoscale in connection with the present invention refers to substances and/or sheet-silicates that have a dimension of 100 nm or less in one direction at least.

Stage b) involves the sheet-silicate being pre swollen; that is, intercalation with, for example, ammonium salts of long-chain fatty amines, alkali metal, alkaline earth metal or boron group cations of higher periods (3rd period or higher) of the periodic table of the elements, or water enlarges the space between the individual lamellae (layers) of the sheet-silicate, this having a decisive influence on the degree of the later exfoliation in the spinning solution. The viscosity of this dispersion increases at the same time. The degree of intercalation is influenced by the size of the intercalated compounds, the amount of intercalated water and also by a defined adjustment of shearing period and shear rate (cf. FIG. 1). The mixing in stage c) preferably takes not more than 15 min and more preferably is carried out for about 10 min.

The organic or inorganic thickeners in step c) comprise nanoparticles on the material basis of fumed silicas, metal oxide ceramics or solvent-compatible metallic nanoparticles and/or aliphatic-aromatic block copolymers. These nonaspectual nanoparticles on the material basis of fumed silicas or metal oxide ceramics may be in an organomodified state.

In addition to controlling the exfoliation of the sheet-silicates to police the release rates for the active ingredients, the sheet-silicates also perform an important role as compatibilizers in the system.

What the inventors found in this connection is that, surprisingly, especially the separate steps b) and c) achieve stable integration of the lipophilic compositions of active ingredients and/or active-containing W/O emulsions into the spinning dope without any further stabilization of the mixtures or encapsulation of the active ingredients being required. They ultimately form a fine dispersion in the shaped article in the form of domains, which is to be understood as meaning regions which are functionally and structurally (quasi)independent of neighboring segments.

It was similarly astonishing and absolutely unforeseeable for a person skilled in the art that the preswelling of the employed sheet-silicate in the separate step b) of the method should allow better control of the degree of exfoliation of the sheet-silicates and hence of the release of the integrated active ingredients and/or W/O emulsion in time and intensity than even the shearing of the mixture of cellulose solution, active ingredient composition and sheet-silicate.

The sheet-silicates in method step b) are preferably organomodified sheet-silicates which, in the galleries of the sheet-silicate platelets, contain organic molecules which promote attachment to the cellulose and simultaneously stabilize the fine state of dispersion of the lipophilic substances (active ingredient compositions) and/or W/O emulsions in the cellulose matrix. But even unmodified sheet-silicates, such as sodium montmorillonite for example, can be used wherever more hydrophilic actives or more preferably W/O emulsions are to be integrated into the cellulose fiber matrix and subsequently released therefrom.

It was found that the degree of intercalation/exfoliation of the sheet-silicates exerts a decisive influence over the firmness of the attachment of the lipophilic substances and/or active ingredient compositions in the cellulose matrix. This can be explained as follows by the construction of sheet-silicates:

Sheet-silicates, as will be known, are constructed of parallel-stacked silicate platelets (individual lamellae), which in turn have a three-ply construction (layer thickness about 1 nm) of alternatingly tetrahedrally and octahedrally coordinated layers of cations which are in a state of interconnection with a conjoint layer of anions. The interlamellar interlayers (galleries) accommodate mobile cations required for charge balance (isomorphous cation exchange in the cation layers) and which in turn are very simple to replace by "organic cations", preferably ammonium or phosphonium cations having at least one longer, unbranched, saturated or unsaturated hydrocarbon moiety having 14 or more carbon atoms, more preferably 14 to 20 carbon atoms, specifically 14, 16 or 18 carbon atoms. The term "unsaturated hydrocarbon moieties" refers to specifically unbranched alkyl moieties having 1, 2 or 3 double bonds. Especially as a result of the intercalation with the recited organic cations having alkyl and/or alkenyl groups, the interlamella interactions, i.e., the cohesion of the individual lamellae, are changed. The alkyl or alkenyl groups may be substituted, especially by hydroxy or carboxy groups. This in turn is reflected in a more or less rapid splitting up into individual lamellae (exfoliation). The same is attained with nonorganomodified sheet-silicates when for example the cations in the galleries, e.g., sodium ions, are exchanged for equivalent cations from higher periods of the periodic table of the elements, e.g., potassium ions, or the sheet-silicates are preswollen in polar solvents such as, for example, water.

Full exfoliation (delamination), i.e., the complete splitting up of the sheet-silicates into silicate platelets (individual lamellae), leads to firm attachment of the lipophilic substances and/or active ingredient compositions to the individual lamellae and in the cellulose matrix, whereas a low degree of exfoliation/intercalation leads to shaped articles which while still containing active ingredients following shaped cellulosic article production give these up relatively rapidly again according to the established degree of exfoliation.

The degree of exfoliation may hence be influenced
  in principle, by the chemical structure and concentration of the organic cations in the sheet-silicate,
  by the size of the intercalated ions or the degree of swelling of nonorganomodified sheet-silicates,
  in steps b) and c), by the temperature, the viscosity of the surrounding medium (dispersant used, moisture and the hydrocarbons used in the stabilized active ingredient mixtures) and also the intensity and duration of the mixing/shearing of the sheet-silicates, and
  in steps b) to d), by the rheological properties of the surrounding medium (hence also the completeness of the cellulose dissolution in the dissolving step), the temperature and likewise the shearing intensity and period.

Where in the case of selected actives (scents, for example) which by dint of excessive volatility and/or thermal and/or chemical sensitivity were not directly integratable into the shaped functional cellulosic article in a fiber-forming and fiber-processing step along the textile supply chain, it was additionally also possible to perform a loading/reloading of the shaped functional articles with active ingredients in effect-relevant amounts.

The inventive fibers, which release active ingredient, are obtainable using any typical dissolving pulps such as hardwood and softwood pulps having high to very high α-cellulose contents (>80%), high-alpha pulps (cotton linters) and also pulps of annual plants with α-contents not less than 90%.

Useful solid or liquid active ingredient compositions for the purposes of the invention may be preferably but not exclusively cosmetic active ingredient compositions such as, for example, evening primrose oil, St John's wort oil, jojoba oil, avocado oil, fat-soluble vitamins and provitamins, such as vitamin A, retinol, vitamin D or vitamin E, active-containing W/O emulsions or apolar plant extracts in concentrations of 0.1 to 200 g per kilogram of cellulose.

The known direct solvents include, for example, NMMO, ionic liquids, or optionally mixtures of organic liquids with the recited direct solvents, or DMAc/LiCl.

The sheet-silicates used are natural and organomodified clay minerals such as, for example, talc, montmorillonite, bentonite or kaolinite and/or synthetic and organomodified silicates such as, for example, Nanofil®, Laponite® or Hectorit®. The sheet-silicate content of the functional cellulosic fiber is in the range from 0.5 to 20%, preferably from 5 to 15% based on the amount of cellulose used.

The highly viscous mixtures of active-containing lipophilic substance, optionally in combination with hydrocarbons and/or the W/O emulsions in method step 1 c) are stabilized using nanoparticles from the material basis of fumed silicas, metal oxide ceramics or solvent-compatible metallic nanoparticles and/or aliphatic-aromatic block copolymers in concentrations of 0.1 to 10% based on the total amount of the mixture of active or active/hydrocarbon or W/O emulsion.

The W/O emulsions are aqueous preparations of active cosmetic ingredients, such as urea, or aqueous extracts of plant ingredients each mixed with apolar hydrocarbons, fatty alcohols, fatty acids and fatty acid esters having more than 8 carbon atoms (in the case of fatty acid esters, more than 8 carbon atoms in the fatty acid portion) and natural or synthetic emulsifiers, wherein the concentrations of the aqueous components is from 0.1 to 200 g per kilogram of emulsion.

The shaped cellulosic articles with inclusions of mixtures of modified sheet-silicates, hydrocarbons and solid or liquid lipophilic actives and/or W/O emulsions according to this method are useful as functional fiber in blend yarns with other natural or manufactured fibers for example of polyester, polyamide, polypropylene, viscose, cotton or wool, in textile knits and wovens with additional functional benefit, in functional nonwovens and functional nonwoven composites, in papers and paper composites and also in functional foils and membranes.

The most important procedures for characterizing the degree of exfoliation of sheet-silicate nanocomposite are x-ray scattering (WAXS) and transmission electron microscopy (TEM). Both procedures, however, have but a limited meaningfulness for a comparative evaluation of the exfoliation of nanocomposite samples. Rheological studies on nanocomposite dispersions offer at least two significant advantages thereover:

i) they interrogate a macroscopic volume of the sample, yet need only a few grams of the sample, and
ii) they are physicochemical standard procedures and experimentally less burdensome than WAXS or TEM.

The procedure rests on the determination of the shear thinning exponent n, which is a semi-quantitative measure of the delamination of a nanophyllosilicate [R. Wagener et al.: "Rheologische Charakterisierung von Nanokompositen", 8. Rudolstädter Kunststofftag, 21 May 2003]. The measurements were carried out in a Haake Mars 2 plate-plate rheometer at small deflections of less than 1%. Preliminary studies were carried out to verify that this shearing amplitude in the measuring instrument does not lead to some unintended orientation of the platelets. The viscosity of the particular samples was measured in the shear rate range between 0.1 and 100 Hz. The flow curve thus obtained was fitted with a power law equation:

$$\eta^* = A \cdot \omega^{(n)},$$

where: $\eta^*$=experimentally determined solution viscosity (or else, in the case of thermoplastic polymers, melt viscosity)
A=pre-exponential factor
$\omega$=oscillation frequency of rheometer (equivalent to shear rate)
n=shear thinning exponent A log-log plot of $\eta^*$ against $\omega$ was used to determine the shear thinning exponent n by placing a straight line against the linear portion of the graph at the lowest shear rates. The value of n is obtained as the slope of the straight line. FIG. 1 shows the result of such a rheological study on cellulose solutions modified with sheet-silicate nanocomposites and subjected to a range of shearing intensities and/or durations.

Values equal to and/or minimally below "0" indicate but a minimal change in the degree of exfoliation. Straight lines having a comparatively large descending slope should be a measure of an increasing exfoliation in the sheet-silicate nanocomposite and indicate an increasingly strong degree of shear thinning. However, shear thinning need not necessarily be the result of differing exfoliation in the nanocomposites, but may also be caused by temperature effects.

For this reason, samples of the composite similar to Example 1 were subjected to a series of measurements at different temperatures in the interval 85° C.<T<115° C. It transpired that in the region of small oscillation frequencies $\omega$<2 Hz there is virtually no effect of the temperature on the flow curve. This behavior of nanocomposites, which is more typical for solids, is evidently determined, as also transpires in studies on, for example, polycarbonate sheet-silicate nanocomposites [P. Pötschke et al., "Rheological behavior of multiwalled carbon nanotube/polycarbonate composites"; Polymer 43:2002, 3247-3255], by a comparatively regular, spatial structure of silicate platelets having strong edge-face interactions.

The methodology described was successfully used to prepare, and semi-quantitatively compare, shaped cellulosic articles where the release of active ingredient is controllable. It has thereby also been possible for the first time for even highly volatile and/or water-soluble actives to be integrated into the final shaped cellulosic article and be released therefrom in a controlled manner.

EXAMPLES

The examples which follow illustrate the invention. They set forth possible embodiments of the method according to the invention without any claim to exclusiveness. Percentages are by mass unless otherwise stated.

Example 1

2.265 kg of cotton linters pulp (DP: 618) and 114 g of propyl gallate are mixed with 21,000 kg of a 60% aqueous NMMO solution and the mixture is sent to a stirred tank. Under agitation by stirring at 50 min$^{-1}$ the furnish is stripped of about 5 l of water in a vacuum of 40 mbar and at a temperature of 50° C. Concurrently, by ULTRATURRAX® homogenizer shearing for 30 min at 25 000 min$^{-1}$, 2.242 kg of an 80% aqueous NMMO solution and 364.5 g of sheet-silicate (montmorillonite modified with methyl-tallow-bis (2-hydroxyethyl)ammonium-cations naturally present in montmorillonite have been exchanged for these ammonium cations=CLOISITE® 30B Nanoclay from Southern Clay) are dispersed and added to the furnish. The furnish batch is further stirred at 50 min$^{-1}$, 100° C. in a vacuum of 20 mbar until a highly viscous mass is formed. The highly viscous mass then has added to it a dispersion of 135 g of evening primrose oil, 545 g of n-octadecane and 91.1 g of fumed silica (AEROSIL® R 106), the dispersion having been fabricated separately under severe ULTRATURRAX® homogenizer shearing, and the entire mixture is further stirred at 100° C. and 20 mbar until homogeneous distribution has been achieved for all components. The shear thinning exponent was determined as −0.86 (curve d) in FIG. 1). After the final spinning dope has been transferred, a dry-wet spinning process (120 µm die orifices, 20 mm air gap) is used to fabricate stable fibers having a fineness of 2.2 dtex and 60 mm cut length.

1500 g of the staple fibers thus fabricated are blended with 3500 g of cotton fibers, the blend is passed through a laboratory card, cross-lapped and needled into a web having a basis weight of 150 g/m$^2$.

To measure the transfer of active ingredient out of the textile fabric onto a technical model of skin, at 25° C. and 60% humidity due to mechanical stress, a rub abrasion tester was used to carry out an actual-wear simulation test in line with DIN EN ISO 105-X12 2002-12. The transferred amount of active ingredient was subsequently detected using HPLC-MS following exhaustive extraction of the skin with toluene. The mean value of 5 replications was 0.073 mg/100 g of evening primrose oil.

The high negative shear thinning exponent found for the spinning solution after having been established by a long shearing time and a high shear rate thus correlates with a very slow release of the incorporated evening primrose oil.

Example 2

A furnish prepared as described in Example 1 had added to it in an otherwise unchanged procedure a dispersion of 135 g of evening primrose oil, 545 g of n-dodecane and 91.1 g of fumed silica (AEROSIL® R 106). The mixture, whose shear thinning exponent n was=−0.56 (curve b) in FIG. 1), is thereafter further treated and shaped similarly to Example 1. The staple fibers obtained were used to produce a web of the same composition and the same basis weight as in Example 1.

A mean value of 0.754 mg/100 g of evening primrose oil was determined on measuring the transfer of active ingredient.

Changing the active ingredient matrix composition leads to a lower negative shear thinning exponent being determined and a faster rate of active ingredient release being attained.

Example 3

A furnish prepared as described in Example 1 had added to it a concurrently fabricated dispersion of 2.242 kg of an 80% aqueous NMMO solution and 364.5 g of sheet-silicate (CLOISITE® 30 B) after ULTRATURRAX® homogenizer dispersion for nearly 10 minutes, and further processed similarly to Example 1. The shear thinning exponent of the solution was −0.67 (curve c) in FIG. 1).

A mean value of 0.522 mg/100 g of evening primrose oil was determined on measuring the transfer of active ingredient.

The distinctly shortened shearing time as compared with Example 1 leads to a reduction in the absolute value of the shear thinning exponent which can be determined and causes a significant increase in the released amount of active ingredient as compared with Example 1.

Example 4

The furnish prepared as described in Example 1 had added to it in am otherwise unchanged procedure a dispersion of 135 g of α-tocopherol, 545 g of palm kernel oil and 91.1 g of fumed silica. The mixture, whose shear thinning exponent was −0.13, is thereafter further treated and shaped similarly to Example 1. The staple fibers obtained were used to produce a web of the same composition and the same basis weight as in Example 1.

A mean value of 1.290 mg/100 g of α-tocopherol was determined on measuring the transfer of active ingredient.

Compared with the examples already described, a change in the composition of the active ingredient matrix with otherwise comparable parameters again causes a distinct increase in the release rate.

Example 5

The furnish prepared as described in Example 1 had added to it in an otherwise unchanged procedure a dispersion of 135 g of W/O emulsion (urea, cocoa butter, wool wax alcohol), 545 g of n-octadecane and 91.1 g of fumed silica (HDE® N 20). The shear chinning exponent was determined as −0.04 (curve a) in FIG. 1). The mixture is thereafter further treated and shaped similarly to Example 1. The staple fibers obtained were used to fabricate a yarn in 30% of functional fibers and 70% of cotton, which was further processed into a fine circular knit piece.

A mean value of 2.680 mg/100 g of urea was determined on measuring the transfer of active ingredient.

W/O emulsions exhibit a very sensitive effect on the shear thinning exponent of the active ingredient matrix composition with otherwise comparable treatment parameters, the lowest shear thinning exponents and comparatively high rates of release.

What is claimed is:

1. A method of producing shaped cellulosic articles featuring controlled release of an active ingredient, said method comprising the stages:
    a) dispersing pulp in an aqueous direct solvent for cellulose to form a cellulose slurry,
    b) in a separate step of the method, forming a shearing dispersion containing a nanoscale sheet silicate and aqueous dirt solvent for cellulose, the nanoscale sheet silicate having been intercalated with either ammonium or phosphonium cations having at least one straight-chain hydrocarbon moiety of 14 or more carbon atoms or preactivated by ion exchange with potassium, calcium or aluminum ions, and intercalating water from the shearing dispersion aqueous direct solvent into the nanoscale sheet silicate during shearing, thereby exfoliating the nanoscale sheet silicate to a controlled degree,
    wherein the degree of exfoliation is influenced by the size of intercalated compounds, the amount of intercalated water, as well as by the length of time and the rate of shearing, and
    adding the sheared nanoscale sheet silicate dispersion of step b) to the cellulose slurry prepared in step a) and mixing it therewith,
    c) in a further separate step of the method, converting a composition of either (i) a lipophilic active ingredient and a lipophilic matrix material which contains the active ingredient or (ii) a lipophilic active ingredient-containing water-in-oil emulsion stabilized by organic or inorganic thickeners into a gel-like paste,
    adding this gel-like paste to the cellulose slurry containing the exfoliated nanoscale sheet silicate dispersion and with mixing at temperatures up to 130° C. therewith under agitation,
    d) removing water after the mixing in step c) to completely dissolve the cellulose and form a spinning solution, and
    e) shaping the resultant spinning solution by a spinning process into shaped articles, after treating and drying, optionally with spin finishing before drying.

2. The method as claimed in claim 1, wherein the aqueous direct solvent for cellulose employed in step a) is an aqueous N-methylmorpholine N-oxide solution, a water-containing ionic liquid, which may further contain organic solvents, or a solution of dimethylacetamide (DMAc) and lithium chloride.

3. The method as claimed in claim 1, wherein the organomodified sheet-silicates are synthetic sheet-silicates modified by ammonium cations having at least one long-chain unbranched alkyl and/or alkenyl moiety of 14 or more carbon atoms, wherein the alkyl or alkenyl moiety may be substituted.

4. The method as claimed in claim 1, wherein the organomodified sheet-silicate(s) is present in the shaped cellulosic articles in a proportion of from 0.5 to 20 wt %, based on the weight of cellulose.

5. The method as claimed in claim 1, wherein the active ingredient is selected from the group of solid or liquid lipophilic active ingredients.

6. The method as claimed in claim 1, wherein the lipophilic matrix material for the active ingredient consists of an apolar hydrocarbon having more than 8 carbon atoms.

7. The method as claimed in claim 1, wherein the inorganic thickeners are nanoparticles of fumed silica, metal oxide ceramic and/or metal.

8. The method as claimed in claim 1, wherein the organic thickeners are aliphatic-aromatic block copolymers.

9. The method as claimed in claim 1, wherein the composition of active ingredient and lipophilic material is present in concentrations of 0.1 to 200 g per kilogram of cellulose.

10. The method as claimed in claim 9, wherein the water-in-oil emulsion comprises a hydrophilic phase dispersed in an oil phase, said hydrophilic phase comprising an aqueous preparation of active cosmetic ingredients or an aqueous extract of plant ingredients, said aqueous preparation or aqueous extract being mixed with apolar hydrocarbons, fatty alcohols, fatty acids, fatty acid esters having more than 8 carbon atoms and natural or synthetic emulsifiers, wherein the concentrations of the aqueous preparation or aqueous extract is from 0.1 to 200 g per kilogram of emulsion.

11. The method as claimed in claim 1, wherein the release of the active ingredients is controlled by the degree of exfoliation of the sheet-silicates, by the chemical structure and the concentration of the cations in the sheet-silicate, by the temperature during the preswelling of the organomodified sheet-silicate and/or during the production of the paste of active ingredient and lipophilic matrix material for the active ingredient, by the viscosity of the dispersant used therein, by the water content therein, by the nature of the lipophilic matrix material and also the intensity and duration of the mixing/shearing of the organomodified sheet-silicates.

12. The method as claimed in claim 1, wherein the organic or inorganic thickeners in step c) are nanoparticles selected from fumed silicas, metal oxide ceramics, solvent-compatible metallic nanoparticles, aliphatic-aromatic block copolymers and combinations thereof, said nanoparticles being present in a proportion of 0.1 to 10 wt %, based on the total weight of the mixture of active ingredient and lipophilic matrix material for the active ingredient.

13. The method as claimed in claim 1, wherein the spinning solution has a shear thinning exponent n in the range from 0.0 to −1.2.

14. The method as claimed in claim 3, wherein the alkyl and/or alkenyl moiety has 14 to 20 carbon atoms and may be substituted with one or more hydroxyl or carboxyl groups.

15. The method as claimed in claim 5, wherein the active ingredient is an active cosmetic ingredients selected from evening primrose oil, St John's wort oil, jojoba oil, avocado oil, fat-soluble vitamins and provitamins, and apolar or aqueous plant extracts.

16. The method as claimed in claim 15, wherein the fat-soluble vitamins and provitamins are vitamin A, retinol, vitamin D or vitamin E.

17. The method as claimed in claim 1, wherein the lipophilic matrix material for the active ingredient is a hydrocarbon that has 8 to 22 carbon atoms and is a (C8-C22)fatty alcohol, a (C8-C22)fatty acid and/or a fatty acid ester having 8 to 22 carbon atoms in the fatty acid portion.

18. The method as claimed in claim 13, wherein the shear thinning exponent n is in the range from −0.1 to −1.0.

19. A method of producing a shaped cellulosic article in claim 1, wherein the active ingredient is contained in a water-in-oil emulsion.

20. The method as claimed in claim 1, wherein the cellulose slurry consists essentially of pulp and aqueous direct solvent, the shaping step comprises shearing, the sheet-silicates comprise organic molecules that stabilize the lipophilic matrix material, and steps b) and c) form domains in the shaped cellulosic article.

21. The method as claimed in claim 1, wherein the lipophilic active ingredient is evening primrose oil, the organic molecule within the sheet-silicates is methyl-tallow-bis(2-hydroxyethyl)ammonium and the lipophilic matrix material is n-octadecane.

* * * * *